US010279106B1

(12) United States Patent
Cook et al.

(10) Patent No.: US 10,279,106 B1
(45) Date of Patent: May 7, 2019

(54) INSULIN PATCH PUMP

(71) Applicant: Tandem Diabetes Care, Inc., San Diego, CA (US)

(72) Inventors: Steven B. Cook, Oceanside, CA (US); Michael Michaud, San Diego, CA (US); Philip Lamb, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 294 days.

(21) Appl. No.: 14/707,851

(22) Filed: May 8, 2015

Related U.S. Application Data

(60) Provisional application No. 61/990,501, filed on May 8, 2014.

(51) Int. Cl.
*A61M 5/142* (2006.01)

(52) U.S. Cl.
CPC ........... *A61M 5/14248* (2013.01); *A61M 2005/14252* (2013.01); *A61M 2005/14268* (2013.01)

(58) Field of Classification Search
CPC .... A61M 5/14248; A61M 2005/14252; A61M 2005/14268; A61M 5/1413; A61M 2005/14573; A61M 2205/0266; A61M 2207/00; A61M 2209/045; A61M 5/14224; A61M 5/1424; A61M 5/1456; A61M 5/158; A61M 5/385
See application file for complete search history.

(56) References Cited

U.S. PATENT DOCUMENTS

| | | | |
|---|---|---|---|
| 4,908,017 A | 3/1990 | Howson et al. |
| 5,665,065 A | 9/1997 | Colman et al. |
| 6,280,408 B1 | 8/2001 | Sipin |
| 6,295,506 B1 | 9/2001 | Heinonen et al. |
| 6,551,276 B1 | 4/2003 | Mann et al. |
| 6,554,798 B1 | 4/2003 | Mann et al. |
| 6,589,229 B1 | 7/2003 | Connelly et al. |
| 6,641,533 B2 | 11/2003 | Causey, III et al. |
| 6,702,779 B2 | 3/2004 | Connelly et al. |
| 6,813,519 B2 | 11/2004 | Lebel et al. |
| 6,872,200 B2 | 3/2005 | Mann et al. |
| 6,936,029 B2 | 8/2005 | Mann et al. |

(Continued)

FOREIGN PATENT DOCUMENTS

| | | |
|---|---|---|
| CN | 101745163 B | 12/2013 |
| WO | WO 2008/103175 A1 | 8/2008 |

(Continued)

*Primary Examiner* — Brandy S Lee
(74) *Attorney, Agent, or Firm* — Patterson Thuente Pedersen, P.A.

(57) ABSTRACT

A user-wearable patch pump system for delivery of insulin or other medicament can include a pump and an attachment portion that attaches the pump to a user's body. The pump can include a drive unit and a disposable cartridge containing a medicament with the drive unit configured to cause the pump to deliver the medicament in the cartridge to the user. The attachment portion can include a retention frame configured to selectively retain the pump therein and an adhesive patch configured to be attached to the user's body. The pump can be selectively attached to the retention frame and used to deliver medicament through tubing to an infusion site displaced from the pump.

22 Claims, 14 Drawing Sheets

(56) References Cited

U.S. PATENT DOCUMENTS

| | | |
|---|---|---|
| 6,940,209 B2 | 9/2005 | Henderson |
| 6,952,604 B2 | 10/2005 | Denuzzio et al. |
| 6,979,326 B2 | 12/2005 | Mann et al. |
| 6,997,920 B2 | 2/2006 | Mann et al. |
| 7,109,878 B2 | 9/2006 | Mann et al. |
| 7,170,214 B2 | 1/2007 | Henderson et al. |
| 7,250,037 B2 | 7/2007 | Shermer et al. |
| 7,309,943 B2 | 12/2007 | Henderson et al. |
| 7,339,306 B2 | 3/2008 | Henderson |
| 7,426,408 B2 | 9/2008 | Denuzzio et al. |
| 7,455,663 B2 | 11/2008 | Bikovsky |
| 7,534,226 B2 | 5/2009 | Mernoe et al. |
| 7,569,050 B2 | 8/2009 | Moberg et al. |
| 7,632,247 B2 | 12/2009 | Adams |
| 7,641,649 B2 | 1/2010 | Moberg et al. |
| 7,682,338 B2 | 3/2010 | Griffin |
| 7,686,787 B2 | 3/2010 | Moberg et al. |
| 7,699,833 B2 | 4/2010 | Moberg et al. |
| 7,708,717 B2 | 5/2010 | Estes et al. |
| 7,713,262 B2 | 5/2010 | Adams et al. |
| 7,717,903 B2 | 5/2010 | Estes et al. |
| 7,736,338 B2 | 6/2010 | Kavazov et al. |
| 7,736,344 B2 | 6/2010 | Moberg et al. |
| 7,744,589 B2 | 6/2010 | Mounce et al. |
| 7,776,030 B2 | 8/2010 | Estes et al. |
| 7,782,192 B2 | 8/2010 | Jeckelmann et al. |
| 7,786,648 B2 | 8/2010 | Xu et al. |
| 7,789,857 B2 | 9/2010 | Moberg et al. |
| 7,794,426 B2 | 9/2010 | Briones et al. |
| 7,794,427 B2 | 9/2010 | Estes et al. |
| 7,794,428 B2 | 9/2010 | Estes et al. |
| 7,794,434 B2 | 9/2010 | Mounce et al. |
| 7,806,868 B2 | 10/2010 | De Polo et al. |
| 7,811,262 B2 | 10/2010 | Moberg et al. |
| 7,815,609 B2 | 10/2010 | Hines et al. |
| 7,819,343 B2 | 10/2010 | Mann et al. |
| 7,828,528 B2 | 11/2010 | Estes et al. |
| 7,828,764 B2 | 11/2010 | Moberg et al. |
| 7,833,196 B2 | 11/2010 | Estes et al. |
| 7,875,022 B2 | 1/2011 | Wenger et al. |
| 7,879,026 B2 | 2/2011 | Estes et al. |
| 7,887,512 B2 | 2/2011 | Estes et al. |
| 7,892,199 B2 | 2/2011 | Mhatre et al. |
| 7,905,868 B2 | 3/2011 | Moberg et al. |
| 7,935,076 B2 | 5/2011 | Estes et al. |
| 7,935,105 B2 | 5/2011 | Miller et al. |
| 7,938,797 B2 | 5/2011 | Estes |
| 7,938,803 B2 | 5/2011 | Mernoe et al. |
| 7,955,305 B2 | 6/2011 | Moberg et al. |
| 7,959,598 B2 | 6/2011 | Estes |
| 7,959,715 B2 | 6/2011 | Kavazov et al. |
| 7,963,954 B2 | 6/2011 | Kavazov |
| 7,976,505 B2 | 7/2011 | Hines et al. |
| 7,981,076 B2 | 7/2011 | Sullivan et al. |
| 7,981,084 B2 | 7/2011 | Estes et al. |
| 7,981,102 B2 | 7/2011 | Patel et al. |
| 7,999,674 B2 | 8/2011 | Kamen |
| 8,032,226 B2 | 10/2011 | Miller et al. |
| 8,062,256 B2 | 11/2011 | Carter et al. |
| 8,095,123 B2 | 1/2012 | Gray |
| 8,105,279 B2 | 1/2012 | Mernoe et al. |
| 8,109,921 B2 | 2/2012 | Estes et al. |
| 8,114,350 B1 | 2/2012 | Silver et al. |
| 8,117,481 B2 | 2/2012 | Anselmi et al. |
| 8,126,728 B2 | 2/2012 | Dicks et al. |
| 8,187,228 B2 | 5/2012 | Bikovsky |
| 8,211,062 B2 | 7/2012 | Estes et al. |
| 8,211,093 B2 | 7/2012 | Miller et al. |
| 8,217,533 B2 | 7/2012 | Jones et al. |
| 8,221,385 B2 | 7/2012 | Estes |
| 8,231,572 B2 | 7/2012 | Carter et al. |
| 8,234,126 B1 | 7/2012 | Estes |
| 8,277,435 B2 | 10/2012 | Estes |
| 8,282,601 B2 | 10/2012 | Mernoe et al. |
| 8,285,328 B2 | 10/2012 | Caffey et al. |
| 8,287,495 B2 | 10/2012 | Michaud et al. |
| 8,287,514 B2 | 10/2012 | Miller et al. |
| 8,299,733 B2 | 10/2012 | Sattler et al. |
| 8,304,960 B2 | 11/2012 | Sattler et al. |
| 8,328,754 B2 | 12/2012 | Estes et al. |
| 8,343,092 B2 | 1/2013 | Rush et al. |
| 8,344,847 B2 | 1/2013 | Moberg et al. |
| 8,408,421 B2 | 4/2013 | DiPerna |
| 8,414,563 B2 | 4/2013 | Kamen et al. |
| 8,444,595 B2 | 5/2013 | Brukalo et al. |
| 8,448,824 B2 | 5/2013 | DiPerna |
| 8,449,523 B2 | 5/2013 | Brukalo et al. |
| 8,450,905 B2 | 5/2013 | Guidarelli et al. |
| 8,451,230 B2 | 5/2013 | Celentano et al. |
| 8,452,953 B2 | 5/2013 | Buck et al. |
| 8,454,557 B1 | 6/2013 | Qi et al. |
| 8,454,562 B1 | 6/2013 | Sims |
| 8,454,575 B2 | 6/2013 | Estes et al. |
| 8,454,581 B2 | 6/2013 | Estes et al. |
| 8,466,637 B2 | 6/2013 | Guidarelli et al. |
| 8,502,662 B2 | 8/2013 | Pohlman et al. |
| 8,517,991 B2 | 8/2013 | Clemente |
| 8,573,027 B2 | 11/2013 | Rosinko et al. |
| 8,601,465 B2 | 12/2013 | Bernstein et al. |
| 8,728,034 B2 | 5/2014 | Yodfat et al. |
| 8,852,152 B2 | 10/2014 | Tverskoy |
| 8,986,253 B2 | 3/2015 | DiPerna |
| 9,362,851 B2 | 6/2016 | Xu et al. |
| 2005/0177111 A1 | 8/2005 | Ozeri et al. |
| 2006/0253086 A1 | 11/2006 | Moberg et al. |
| 2007/0073236 A1 | 3/2007 | Mernoe et al. |
| 2007/0156092 A1 | 7/2007 | Estes et al. |
| 2007/0167905 A1 | 7/2007 | Estes et al. |
| 2007/0167912 A1 | 7/2007 | Causey et al. |
| 2007/0173762 A1 | 7/2007 | Estes et al. |
| 2007/0179444 A1 | 8/2007 | Causey et al. |
| 2008/0045902 A1 | 2/2008 | Estes et al. |
| 2008/0045903 A1 | 2/2008 | Estes et al. |
| 2008/0045904 A1 | 2/2008 | Estes et al. |
| 2008/0045931 A1 | 2/2008 | Estes et al. |
| 2008/0051697 A1 | 2/2008 | Mounce et al. |
| 2008/0051698 A1 | 2/2008 | Mounce et al. |
| 2008/0051709 A1 | 2/2008 | Mounce et al. |
| 2008/0051711 A1* | 2/2008 | Mounce ............... A61J 1/1406 604/131 |
| 2008/0051716 A1 | 2/2008 | Stutz |
| 2008/0051727 A1 | 2/2008 | Moberg et al. |
| 2008/0051765 A1 | 2/2008 | Mounce |
| 2008/0097291 A1 | 4/2008 | Hanson et al. |
| 2008/0097327 A1 | 4/2008 | Bente et al. |
| 2008/0097375 A1 | 4/2008 | Bikovsky |
| 2008/0097381 A1 | 4/2008 | Moberg et al. |
| 2008/0215035 A1 | 9/2008 | Yodfat et al. |
| 2008/0269680 A1 | 10/2008 | Ibranyan et al. |
| 2008/0269681 A1 | 10/2008 | Kavazov et al. |
| 2008/0269682 A1 | 10/2008 | Kavazov et al. |
| 2008/0294094 A1 | 11/2008 | Mhatre et al. |
| 2008/0294108 A1 | 11/2008 | Briones et al. |
| 2008/0294109 A1 | 11/2008 | Estes et al. |
| 2008/0294142 A1 | 11/2008 | Patel et al. |
| 2009/0036870 A1 | 2/2009 | Mounce et al. |
| 2009/0067989 A1 | 3/2009 | Estes et al. |
| 2009/0069745 A1 | 3/2009 | Estes et al. |
| 2009/0069746 A1 | 3/2009 | Miller et al. |
| 2009/0069749 A1 | 3/2009 | Miller et al. |
| 2009/0069784 A1 | 3/2009 | Estes et al. |
| 2009/0069785 A1 | 3/2009 | Miller et al. |
| 2009/0069787 A1 | 3/2009 | Estes et al. |
| 2009/0082728 A1 | 3/2009 | Bikovsky |
| 2009/0124994 A1 | 5/2009 | Roe |
| 2009/0156990 A1 | 6/2009 | Wenger et al. |
| 2009/0171324 A1 | 7/2009 | Chong et al. |
| 2009/0254037 A1 | 10/2009 | Bryant, Jr. et al. |
| 2009/0259183 A1 | 10/2009 | Chong et al. |
| 2009/0259198 A1 | 10/2009 | Chong et al. |
| 2009/0259209 A1 | 10/2009 | Chong et al. |
| 2009/0270811 A1 | 10/2009 | Mounce et al. |
| 2009/0275887 A1 | 11/2009 | Estes |
| 2009/0287180 A1 | 11/2009 | DiPerna |

(56) References Cited

U.S. PATENT DOCUMENTS

| | | |
|---|---|---|
| 2009/0326458 A1 | 12/2009 | Chong et al. |
| 2010/0008795 A1 | 1/2010 | DiPerna |
| 2010/0016791 A1 | 1/2010 | Chong et al. |
| 2010/0049164 A1 | 2/2010 | Estes |
| 2010/0071446 A1 | 3/2010 | Brown |
| 2010/0094251 A1 | 4/2010 | Estes |
| 2010/0152658 A1 | 6/2010 | Hanson et al. |
| 2010/0152674 A1 | 6/2010 | Kavazov et al. |
| 2010/0174266 A1 | 7/2010 | Estes |
| 2010/0185142 A1 | 7/2010 | Kamen et al. |
| 2010/0185175 A1 | 7/2010 | Kamen et al. |
| 2010/0198183 A1 | 8/2010 | Lanigan et al. |
| 2010/0218586 A1 | 9/2010 | Rosinko et al. |
| 2010/0228186 A1 | 9/2010 | Estes et al. |
| 2010/0241065 A1 | 9/2010 | Moberg et al. |
| 2010/0331824 A1 | 12/2010 | Moberg et al. |
| 2011/0006876 A1 | 1/2011 | Moberg et al. |
| 2011/0009725 A1 | 1/2011 | Hill et al. |
| 2011/0009813 A1 | 1/2011 | Rankers |
| 2011/0009823 A1 | 1/2011 | Chong et al. |
| 2011/0009825 A1 | 1/2011 | Chong et al. |
| 2011/0030845 A1 | 2/2011 | Chong et al. |
| 2011/0040247 A1 | 2/2011 | Mandro et al. |
| 2011/0047499 A1 | 2/2011 | Mandro et al. |
| 2011/0082439 A1 | 4/2011 | Wenger et al. |
| 2011/0105955 A1 | 5/2011 | Yudovsky et al. |
| 2011/0112504 A1 | 5/2011 | Causey et al. |
| 2011/0118662 A1 | 5/2011 | Mhatre et al. |
| 2011/0160650 A1 | 6/2011 | Chong et al. |
| 2011/0160654 A1 | 6/2011 | Hanson et al. |
| 2011/0160666 A1 | 6/2011 | Hanson et al. |
| 2011/0160678 A1 | 6/2011 | Chong et al. |
| 2011/0178461 A1 | 7/2011 | Chong et al. |
| 2011/0190694 A1 | 8/2011 | Lanier, Jr. et al. |
| 2011/0190700 A1 | 8/2011 | Kavazov et al. |
| 2011/0192478 A1 | 8/2011 | Chong et al. |
| 2011/0213306 A1 | 9/2011 | Hanson et al. |
| 2011/0213329 A1* | 9/2011 | Yodfat ............... A61M 5/14248 604/500 |
| 2012/0029708 A1 | 2/2012 | Miller et al. |
| 2012/0123230 A1 | 5/2012 | Brown et al. |
| 2012/0185267 A1 | 7/2012 | Kamen et al. |
| 2012/0203178 A1 | 8/2012 | Tverskoy |
| 2013/0012917 A1 | 1/2013 | Miller et al. |
| 2013/0053816 A1 | 2/2013 | DiPerna et al. |
| 2013/0159456 A1 | 6/2013 | Daoud et al. |
| 2013/0283196 A1 | 10/2013 | Farnan et al. |
| 2013/0306191 A1 | 11/2013 | Metzmaker et al. |
| 2013/0324920 A1 | 12/2013 | Kohli et al. |
| 2013/0324928 A1 | 12/2013 | Kruse |
| 2013/0331778 A1 | 12/2013 | Kruse et al. |
| 2013/0331790 A1 | 12/2013 | Brown et al. |
| 2013/0332874 A1 | 12/2013 | Rosinko et al. |
| 2014/0054883 A1* | 2/2014 | Lanigan ............. A61M 39/1011 285/33 |
| 2014/0273042 A1 | 9/2014 | Saint |
| 2014/0276409 A1 | 9/2014 | Rosinko et al. |
| 2014/0276419 A1 | 9/2014 | Rosinko et al. |
| 2014/0276420 A1 | 9/2014 | Rosinko |
| 2014/0276423 A1 | 9/2014 | Lecanu-Fayet |
| 2014/0276531 A1 | 9/2014 | Walsh |
| 2014/0276537 A1 | 9/2014 | Kruse |
| 2014/0276538 A1 | 9/2014 | Michaud |
| 2014/0276553 A1 | 9/2014 | Rosinko et al. |
| 2014/0276556 A1 | 9/2014 | Saint et al. |
| 2014/0276569 A1 | 9/2014 | Kruse |
| 2014/0276570 A1 | 9/2014 | Saint |
| 2014/0276571 A1 | 9/2014 | Ludolph |
| 2014/0276574 A1 | 9/2014 | Saint |
| 2014/0296784 A1* | 10/2014 | Lopez ................. A61M 5/1413 604/151 |
| 2014/0378898 A1 | 12/2014 | Rosinko |
| 2015/0072613 A1 | 3/2015 | Swanson |
| 2015/0073337 A1 | 3/2015 | Saint et al. |
| 2015/0182695 A1 | 7/2015 | Rosinko et al. |
| 2016/0136357 A1 | 5/2016 | Yang |
| 2016/0157759 A1 | 6/2016 | Yang |
| 2016/0157765 A1 | 6/2016 | Zhu |
| 2016/0158436 A1 | 6/2016 | Yang |
| 2016/0199572 A1 | 7/2016 | Yang |
| 2016/0339197 A1 | 11/2016 | Michaud et al. |
| 2017/0049957 A1 | 2/2017 | Michaud |
| 2017/0290976 A1 | 10/2017 | Murphy et al. |

FOREIGN PATENT DOCUMENTS

| | | |
|---|---|---|
| WO | WO 2008/144693 A1 | 11/2008 |
| WO | WO 2008/144695 A1 | 11/2008 |
| WO | WO 2008/144697 A1 | 11/2008 |
| WO | WO 2008/144698 A1 | 11/2008 |
| WO | WO 2009/013736 A1 | 1/2009 |
| WO | WO 2009/016636 A2 | 2/2009 |
| WO | WO 2009/032399 A1 | 3/2009 |
| WO | WO 2009/032400 A1 | 3/2009 |
| WO | WO 2009/032402 A1 | 3/2009 |
| WO | WO 2009/035759 A1 | 3/2009 |

* cited by examiner

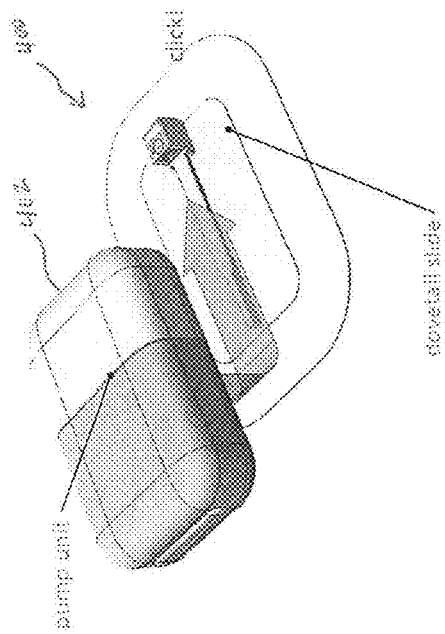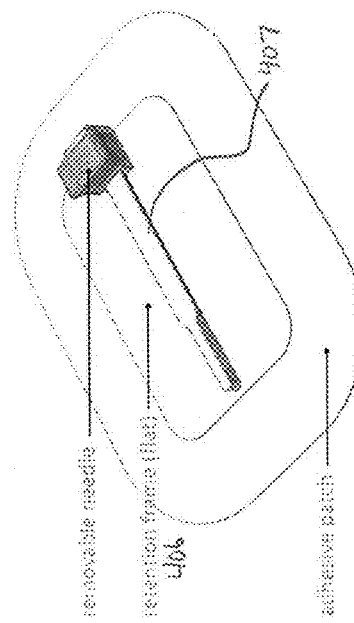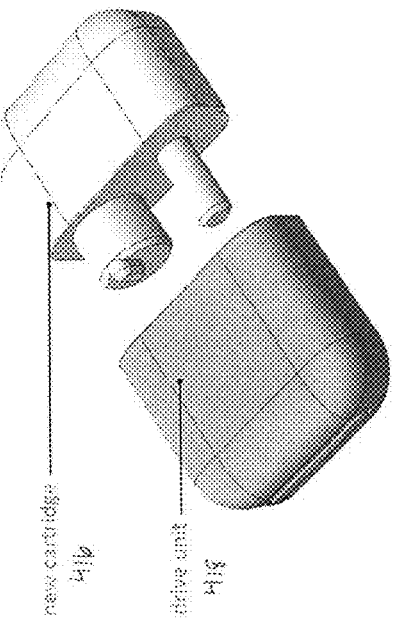

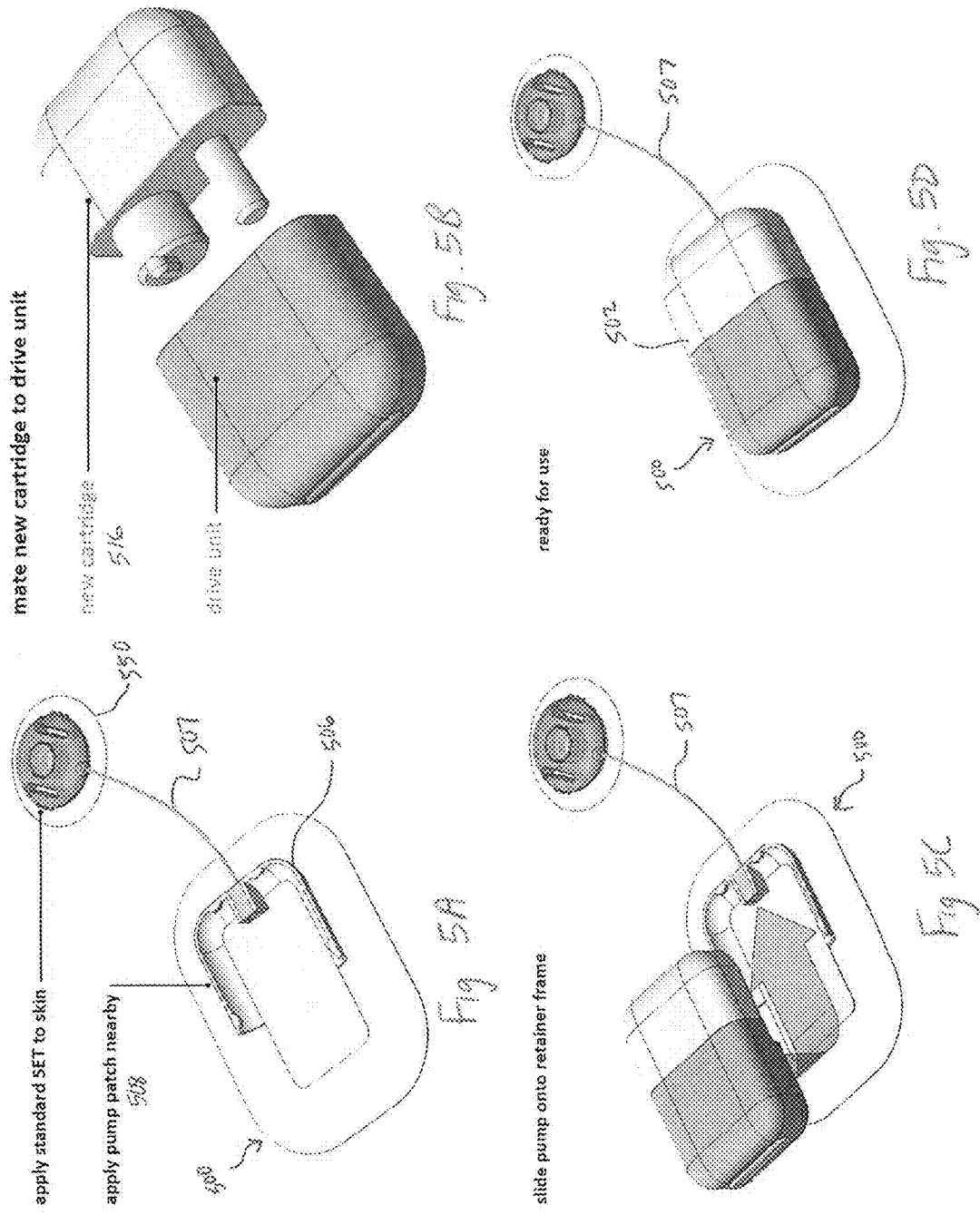

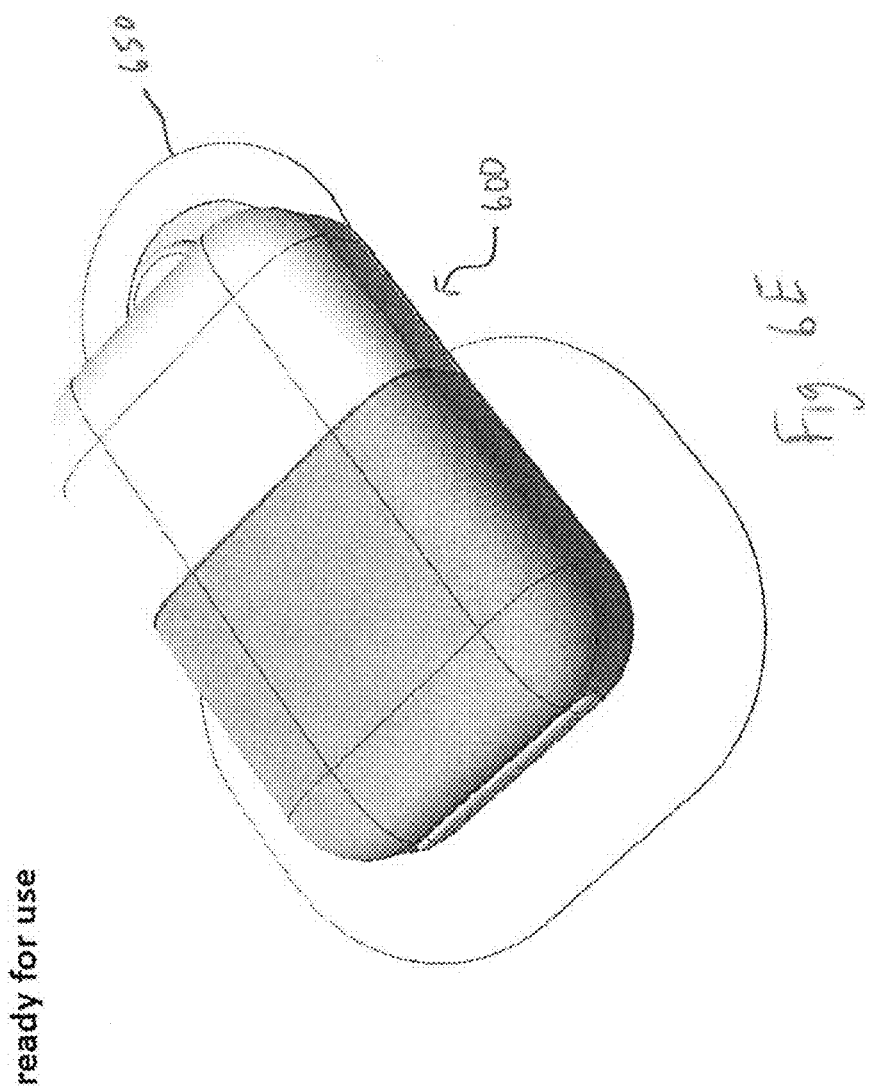

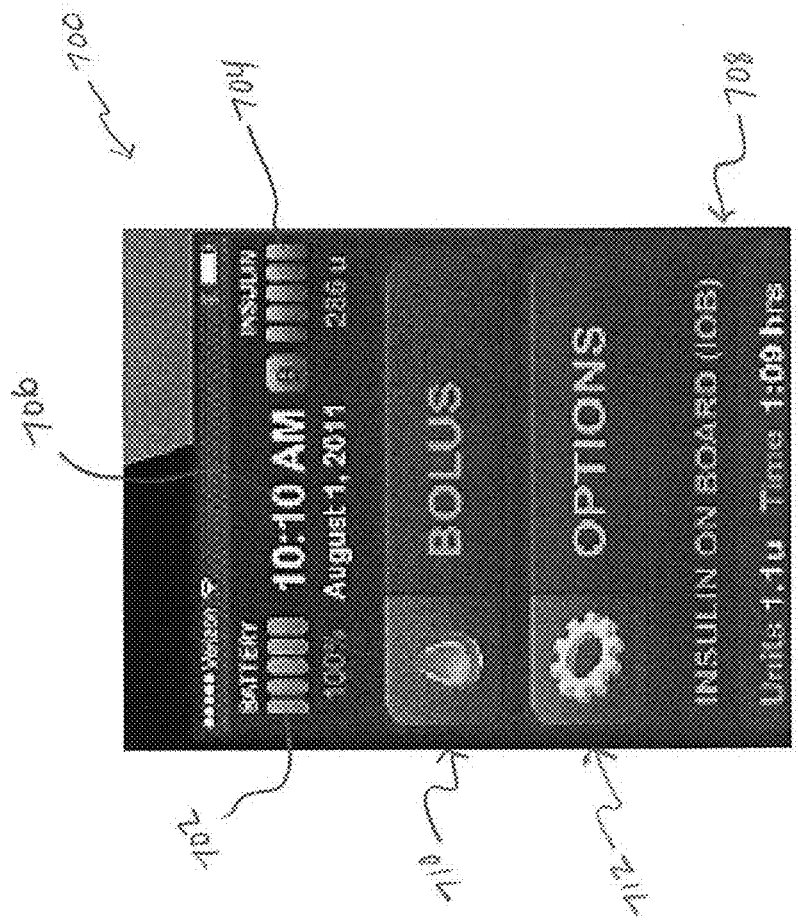

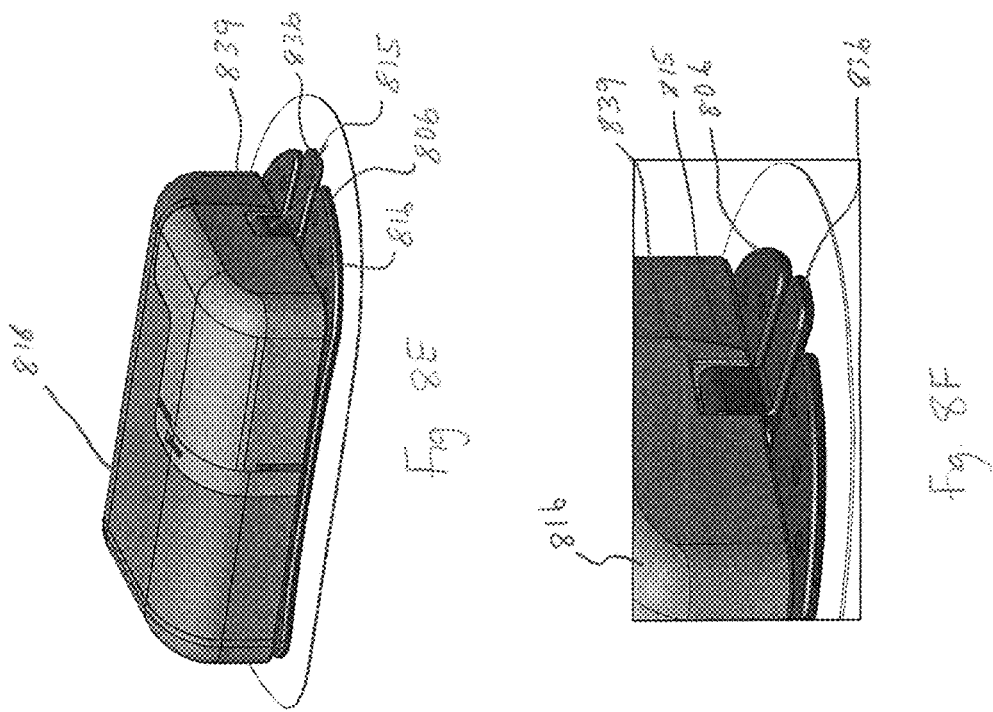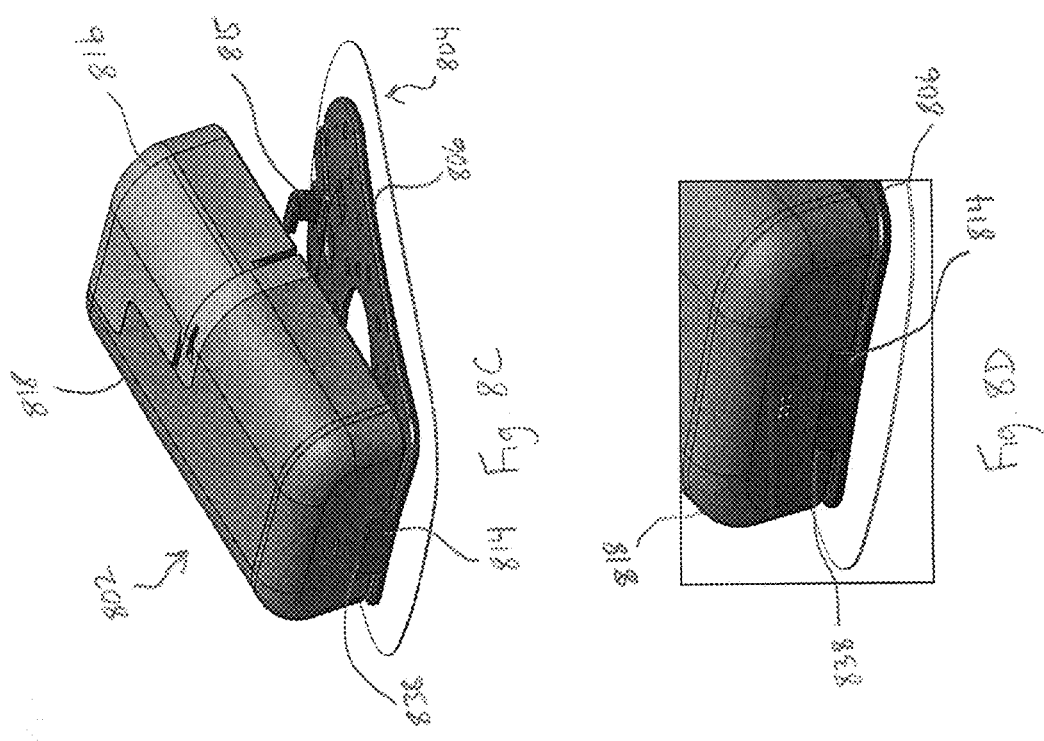

INSULIN PATCH PUMP

RELATED APPLICATION

The present application claims the benefit of U.S. Provisional Application No. 61/990,501 filed May 8, 2014, which is incorporated herein in its entirety by reference.

FIELD OF THE INVENTION

The present invention relates to medical pumps for delivering medicament to a patient and, more specifically, to a user-wearable insulin patch pump for delivering insulin to a patient.

BACKGROUND OF THE INVENTION

There are many applications in academic, industrial, and medical fields that benefit from devices and methods that are capable of accurately and controllably delivering fluids, such as liquids and gases, that have a beneficial effect when administered in known and controlled quantities. Such devices and methods can be particularly useful in the medical field where treatments for many patients include the administration of a known amount of a substance at predetermined intervals.

One category of devices for delivering such fluids is that of pumps that have been developed for the administration of insulin and other medicaments for those suffering from both type I and type II diabetes. Some pumps configured as portable infusion devices can provide continuous subcutaneous medicament injection and/or infusion therapy for the treatment of diabetes. Such therapy may include, e.g., the regular and/or continuous injection or infusion of insulin into the skin of a person suffering from diabetes and offer an alternative to multiple daily injections of insulin by an insulin syringe or an insulin pen. Such pumps can be ambulatory/portable infusion pumps that are worn by the user and may use replaceable cartridges. Examples of such pumps and various features that can be associated with such pumps include those disclosed in U.S. patent application Ser. No. 13/557,163, U.S. patent application Ser. No. 12/714,299, U.S. patent application Ser. No. 14/538,018, U.S. patent application Ser. No. 13/838,617, U.S. patent application Ser. No. 13/827,707 and U.S. Pat. No. 8,287,495, each of which is hereby incorporated herein by reference in its entirety.

One type of pump that has been developed is a patch pump, or micro pump. Patch pumps are small pumps, typically ambulatory, that are carried directly on the skin under the user's clothing. Such a pump generally is situated directly on the injection site such that no tubing is required to deliver the insulin or other medicament to the patient. Patch pumps typically are at least in part disposable, meant to be worn for a day or two and then discarded for a new patch pump.

SUMMARY

A user-wearable patch pump system for delivery of insulin or other medicament can include a pump and an attachment portion that attaches the pump to a user's body. The pump can include a drive unit and a disposable cartridge containing a medicament with the drive unit configured to cause the pump to deliver the medicament in the cartridge to the user. The attachment portion can include a retention frame configured to selectively retain the pump therein and an adhesive patch configured to be attached to the user's body.

In one embodiment, the user-wearable patch pump system can include both tubing configured to extend between the retention frame and an infusion site displaced from the retention frame and a cannula configured to extending into an infusion site directly beneath the retention frame. In such an embodiment, the pump can be selectively attached to the retention frame and used to deliver medicament either through the cannula to the infusion site directly beneath the retention frame or through the tubing to the infusion site displaced from the retention frame. Such a configuration provides the user with the flexibility of using multiple infusion sites with a single point of attachment of the pump on the body.

In some embodiments, the retention frame can include a sealing membrane. The sealing membrane can provide an opening through the frame configured to receive a removable needle for insertion of a cannula that can be used to deliver medicament. In other embodiments, the retention frame can include a receiving slot configured to receive a connector of a standard infusion set. In such embodiments, the cannula of the infusion set can then be used to deliver medicament.

In various embodiments, the pump can attach to and be retained by the frame in a variety of different ways. In some embodiments, the pump is mated with the retention frame in a generally vertical manner to cause one or more tabs on the frame to snap into engagement with one or more recesses on the pump. In one such embodiment, the frame includes a first tab configured as a hook portion and a second tab configured as a snap portion. The pump can be engaged with the frame by first inserting a first recess in the pump onto the hook portion and then rotating the pump downwardly about the hook portion to engage a second recess in the pump with the snap portion. In other embodiments, the pump can be generally horizontally, slidably received by the frame, such as by engaging elongate recesses along the sides of the pump with elongate tabs on the frame or by engaging an elongate recess on a bottom of the pump with an elongate upwardly extending projection on the frame. In a further embodiment, the frame can include a rotatable cleat such that engaging a recess on the pump with the cleat and then turning the pump on the cleat locks the pump onto the frame.

Certain embodiments are described further in the following description, examples, claims, and drawings. These embodiments will become more apparent from the following detailed description when taken in conjunction with the accompanying exemplary drawings.

BRIEF DESCRIPTION OF THE DRAWINGS

FIGS. 4A-4F are perspective views of portions of a patch pump system according to an embodiment of the present invention.

FIGS. 5A-5D are perspective views of portions of a patch pump system according to an embodiment of the present invention.

FIGS. 6A-6E are perspective views of portions of a patch pump system according to an embodiment of the present invention.

FIG. 7 is a screen shot of a control screen for a control device for controlling a patch pump according to an embodiment of the present invention.

FIGS. 8A-8F are views of portions of a patch pump system according to an embodiment of the present invention.

DETAILED DESCRIPTION OF THE DRAWINGS

FIGS. 1A-1F depict a patch pump 100 according to one embodiment of the invention. Patch pump 100 includes a pump 102 and an attachment portion 104 that enables the attachment of the pump 104 to the user.

Figure 1A:
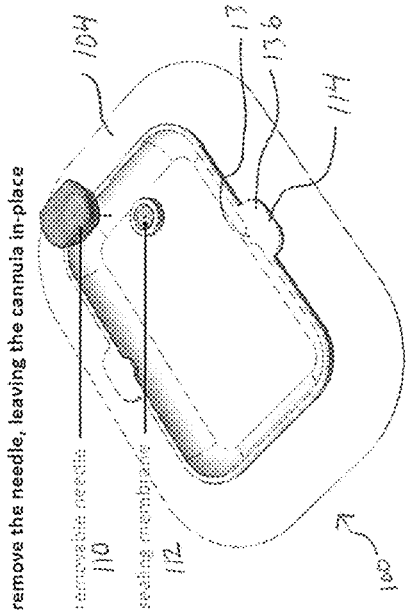
FIGS. 1A-1F are perspective views of portions of a patch pump system according to an embodiment of the present invention.
Figure 1B:
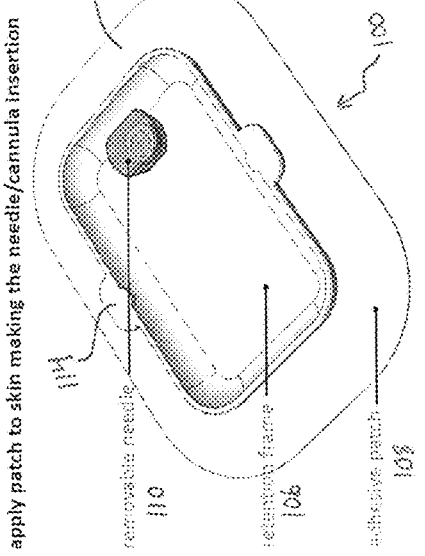

The attachment portion 104 of patch pump, depicted most clearly in FIGS. 1A and 1B, includes a retention frame 106 affixed to an adhesive patch 108 and a removable needle 110. In one embodiment, the retention frame 106 is preattached to the adhesive patch 108 with, for example, glue or other suitable adhesive or technique. In other embodiments, the retention frame 106 can be removably attachable with the adhesive patch 108 or can be permanently attached to the retention frame 106 by the user. In certain embodiments, the retention frame 106 can comprise polypropylene, polycarbonate or Cyclic Insulin Copolymer (COC). In general, retention frame 106 can comprise any flexible and fatigue-resistant material.

In this embodiment, the retention frame 106 includes a seal membrane 112 near an end of the frame 106, a pair of tabs 114 along each side of the frame 106 and a removable needle 110. The sealing membrane 112 initially interfaces with the removable needle 110. When the attachment portion 104 is positioned on the user's body, the removable needle 110, as extended through the sealing membrane 112, penetrates the user's skin to insert a cannula 130 (shown in FIG. 1F) through the user's skin. The removable needle 110 can then be removed and discarded. As will be described herein, the sealing membrane 112 will interface with the pump for delivering medicament such as, e.g., insulin, from the pump 102 to the patient through the cannula 130.

Figure 1C:
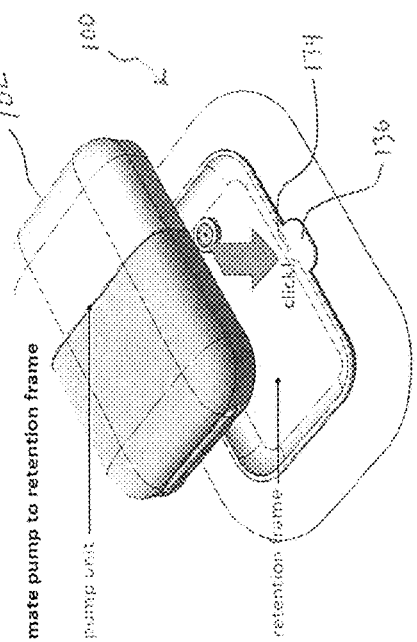

The pump 102 includes a cartridge 116 and a drive unit 118 that mate together to form the pump 102. Cartridge 116 is generally a disposable unit containing medicament such as insulin and a drive unit 118 in operation interfaces with cartridge 116 to cause medicament such as insulin from the cartridge to be delivered to the patient. As can be seen in FIG. 1C, cartridge 116 can include an electrical contact 120 for electrically connecting the cartridge 116 and the drive unit 118 and a drive mechanism 122 that mechanically interconnects the cartridge 116 with the drive unit 118 to enable to drive unit 118 to cause insulin to be delivered from the cartridge 116. The drive unit, as shown in FIG. 1F, can include corresponding recesses 124, 126 for accepting the electrical contact 120 and the drive mechanism 122, respectively. Cartridge also includes an opening 128 in a bottom of the cartridge that is aligned with the sealing membrane 112 of the retention frame 106, thereby aligning a cartridge cannula 132 with cannula 130 of the attachment portion 104. In certain embodiments, the drive unit and cartridge can be comprised of, for example, polypropylene, polycarbonate COC, or any other flexible and fatigue-resistant material. Although pump 102 may generally be controlled with a remote device such as, e.g., a smartphone, as described herein, pump 102 may also include a bolus key 140, shown here presented on the drive unit 118, for delivering a predetermined quantity of insulin with each push of the key 140.

Figure 1D:
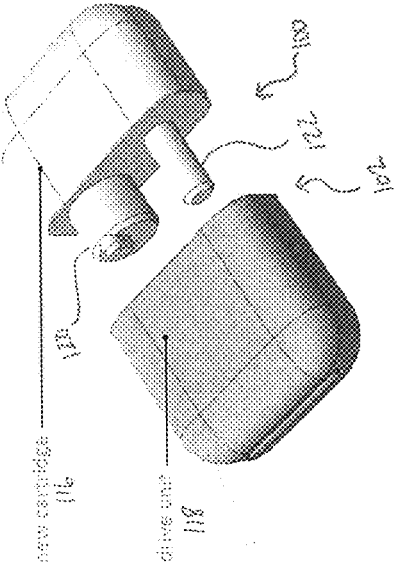
Figure 1F:
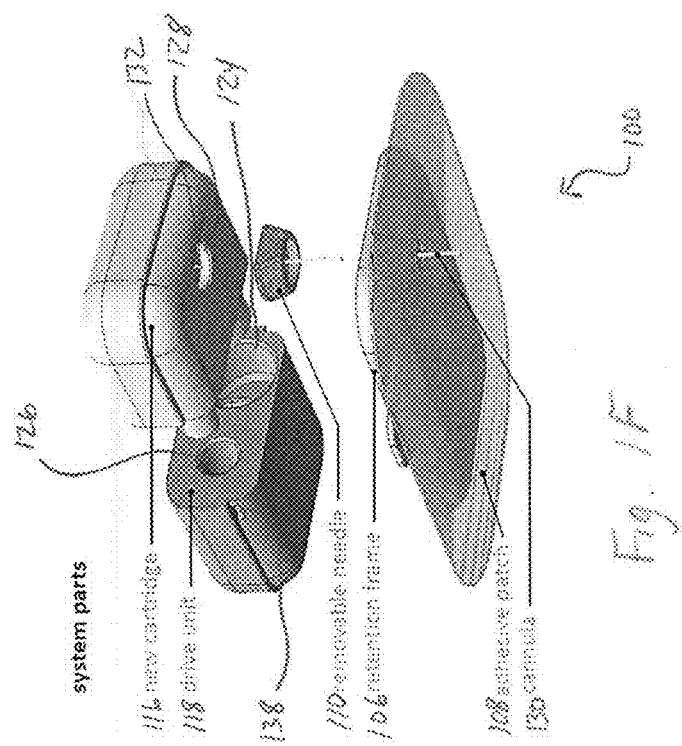
Figure 1E:
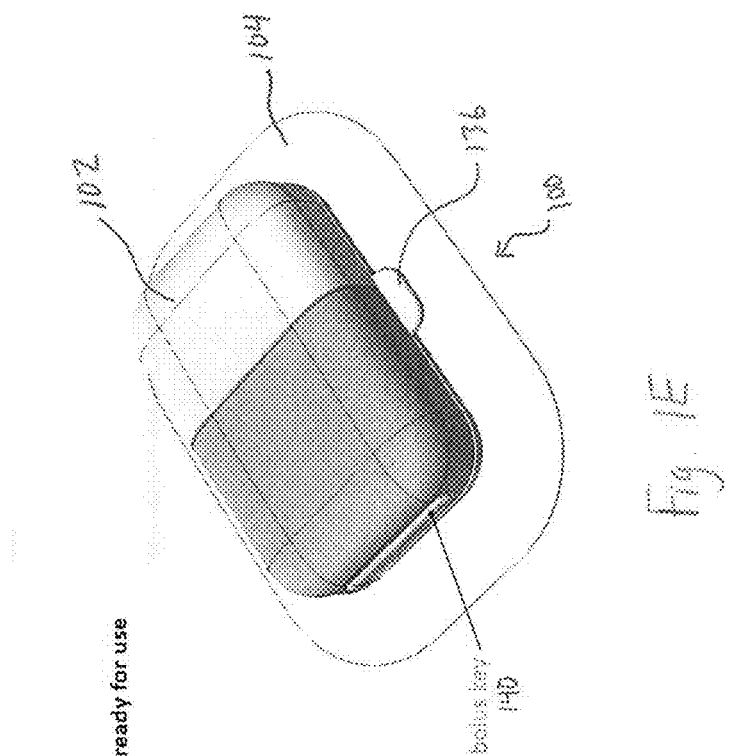
Figure 2B:
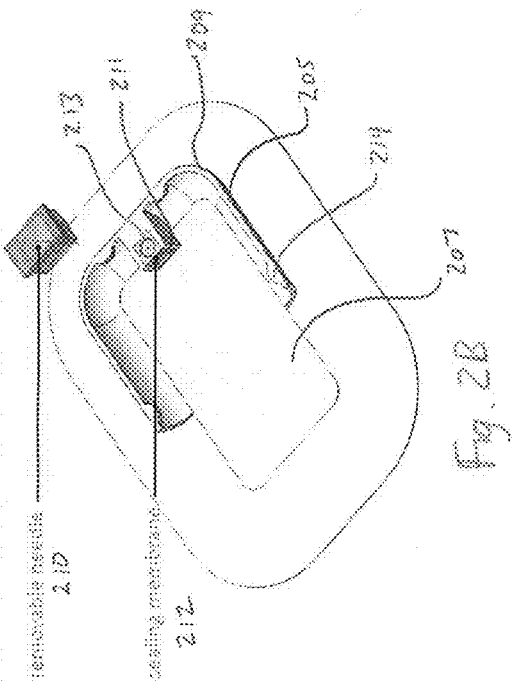
FIGS. 2A-2F are perspective views of portions of a patch pump system according to an embodiment of the present invention.
Figure 2D:
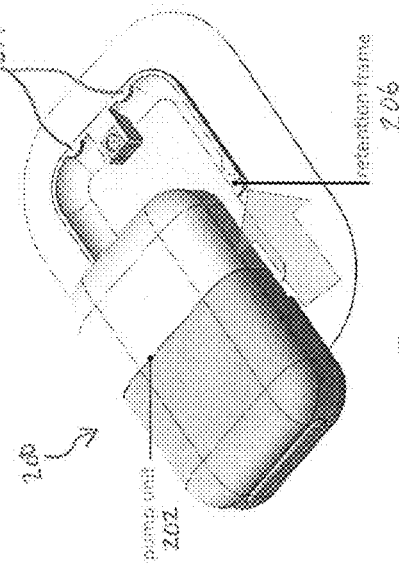
Figure 2A:
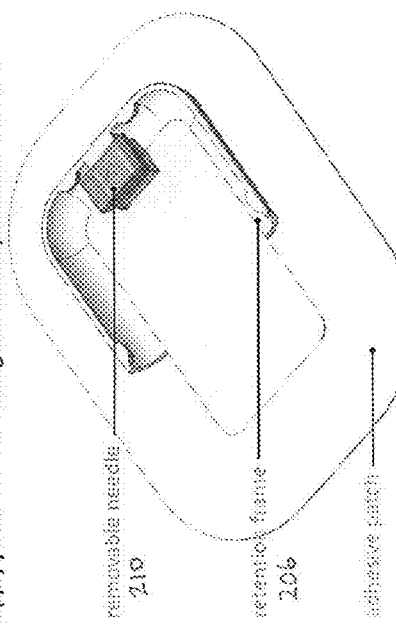
Figure 2C:
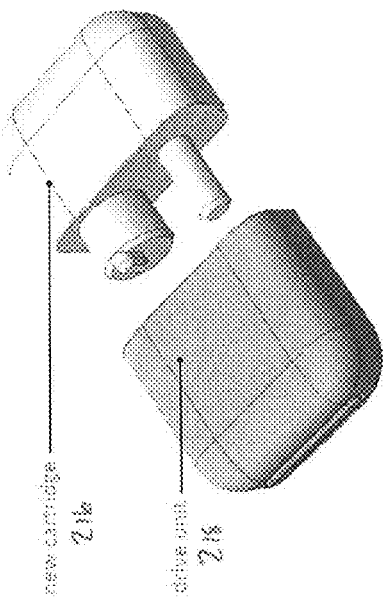
Figure 2F:
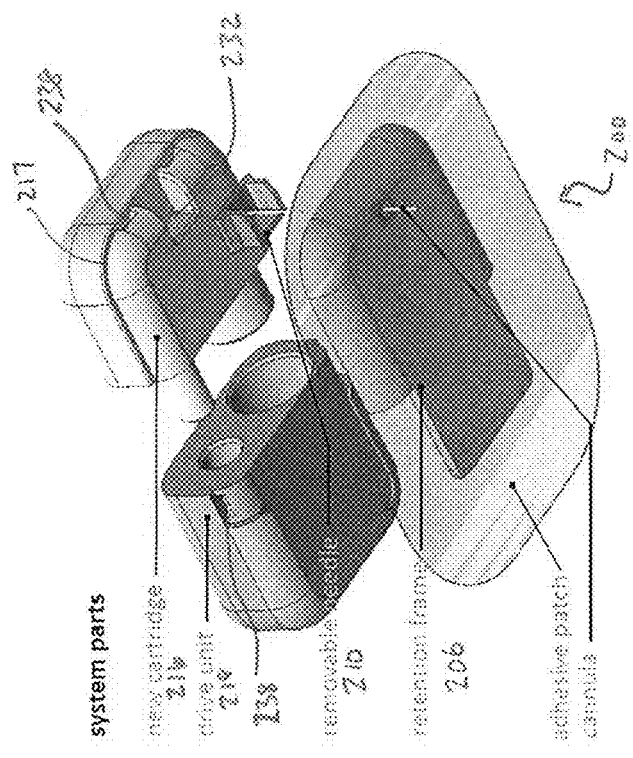
Figure 2E:
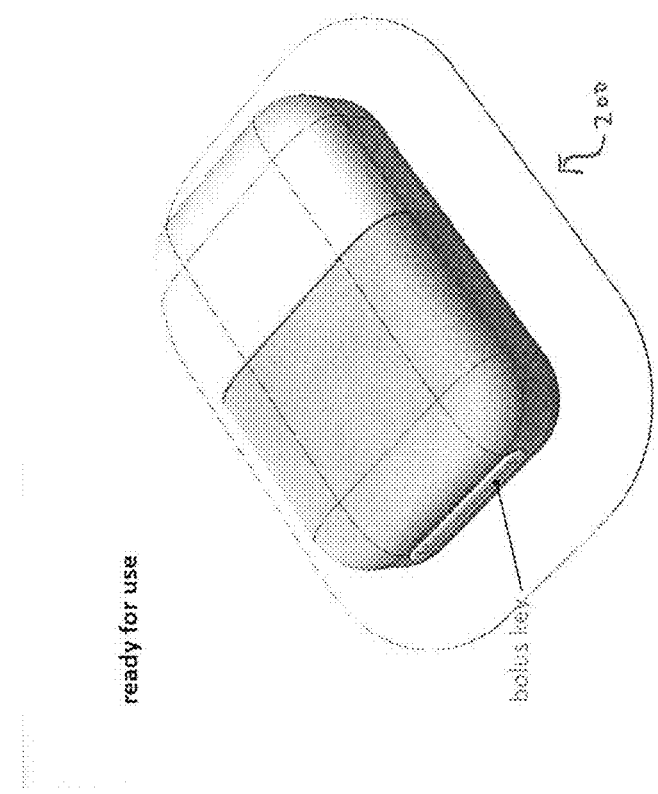

As shown in FIG. 1D, pump 102 is mated with the retention frame 106 by aligning the pump 102 with the retention frame 106 and pushing it downward onto the frame. Tabs 114 of frame include smaller inner wings 134 and larger outer wings 136. When the pump 102 is pressed downwardly onto the frame 106, the inner wings 134 snap into corresponding recesses 138 on the sides of the pump 102, mechanically locking the pump 102 in place on the frame 106 so it will not inadvertently become dislodged. This snapping action may create an audible "clicking" sound to indicate to the user that the pump 102 is properly mated to the frame 106. As shown, the recesses 138 may be on the drive unit 118. Alternatively, the recesses 138 can be positioned on the cartridge 116. In a further alternative, the recesses 138 can be partially on each of the drive unit 118 and cartridge 116, thereby serving not only to retain the pump 102 on the retention frame 106, but also to provide a further measure holding the two aspects of the pump 102 together. To remove the pump 102 from the cartridge, the outer wings 136 can be pressed downwardly, which will cause the inner wings 134 to slide out from the recesses 138, releasing the pump.

FIGS. 2A-2F depict a patch pump 200 according to another embodiment of the present invention. Patch pump 200 includes similar components to patch pump 100 of FIGS. 1A-1F, and therefore, as with the further embodiments described herein, identical components and functions may not be further described with respect to this embodiment. In this embodiment, the retention frame 206 comprises a surface 207 sized to accommodate the pump 202 and a half clamshell retaining feature 209. The retention frame 206 includes a sealing membrane 212 having a different configuration from sealing membrane 112 of FIGS. 1A-1F and a removable needle 210 shaped to interface with the sealing membrane 212. Note that when the pump 202 is mated with the retention frame 206, the cartridge cannula 232 extends longitudinally into a cartridge opening 211 of the sealing membrane 212 that is different from and aligned perpendicularly to the needle opening 213 through which the needle is inserted.

The pump 202 is attached to the retention frame 206 in this embodiment by a horizontal sliding motion, rather than a vertical motion as with pump 102 and retention frame 106 of the previous embodiment. Retention frame 206 includes a plurality of inwardly projecting tabs 214. These tabs 214 mate with corresponding recesses 238 in the cartridge 216 and/or drive unit 218 of the pump 202 to retain the pump 202 on the retention frame 206. Cartridge 216 can include an undercut portion 217 that slidably mates with the upper rim 205 of retention frame, which creates a smooth outer profile for the combination of the pump 202 and retention frame 206. In other embodiments, the undercut portion 217 can extend onto a portion of drive unit 218 as well. Pump 202 is therefore retained on retention frame 206 primarily by a friction fit, so the pump 202 can be removed by a horizontal force in the opposite direction that overcomes this friction.

Figure 3A:
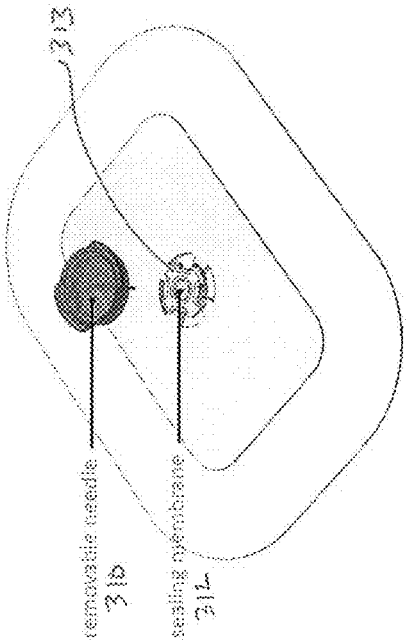
FIGS. 3A-3F are perspective views of portions of a patch pump system according to an embodiment of the present invention.
Figure 3B:
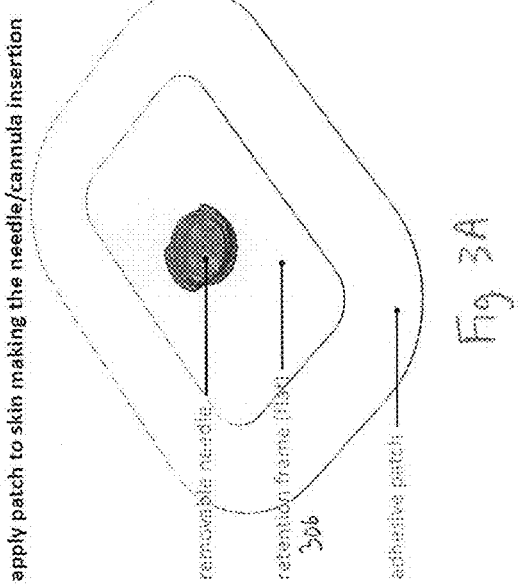
Figure 3C:
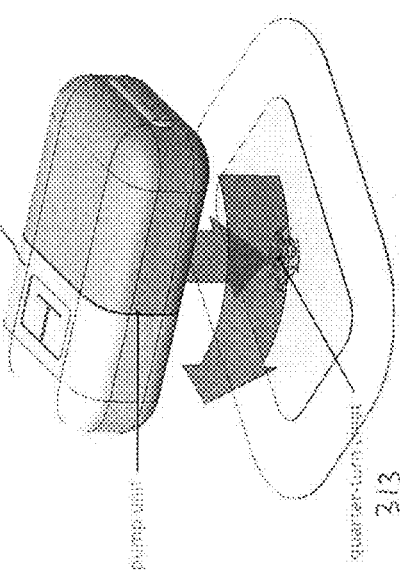
Figure 3D:
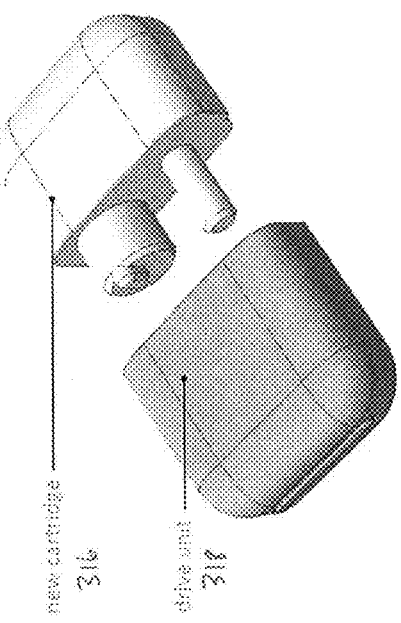
Figure 3E:
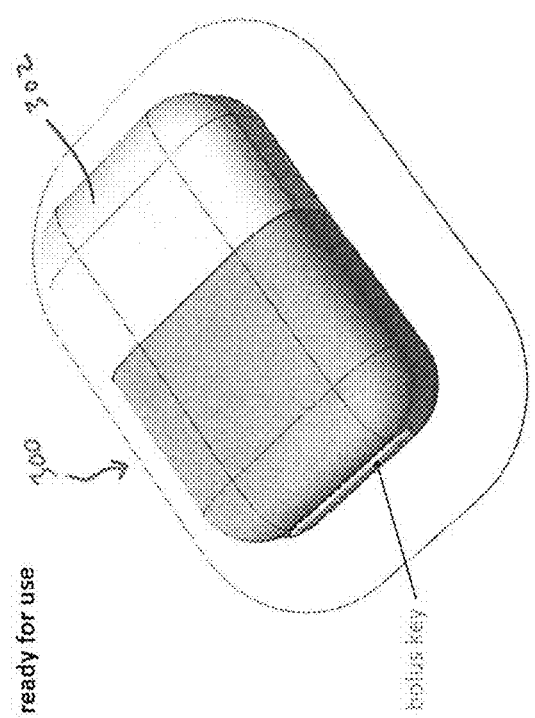
Figure 3F:
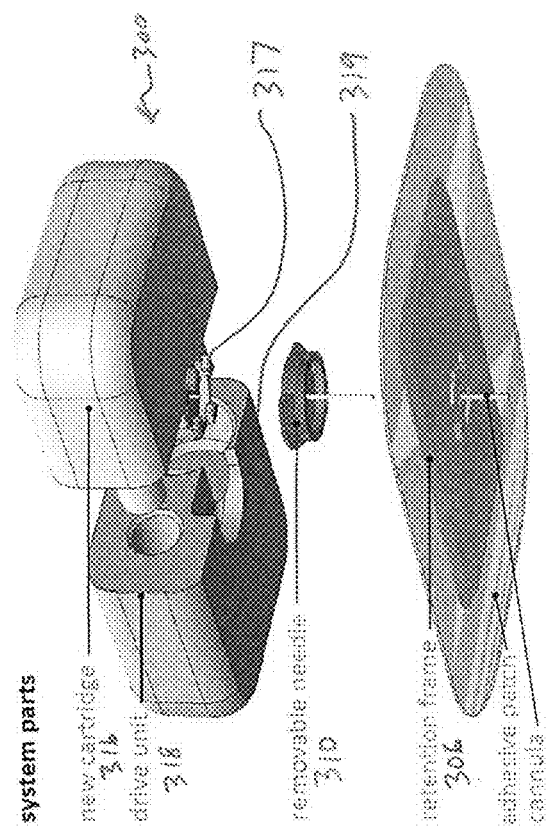

Referring now to FIGS. 3A-3F, there can be seen an insulin patch pump 300 according to another embodiment of the invention. In this embodiment, the sealing membrane 312 is positioned generally centrally on a generally flat retention frame 306. After the insertion needle 310 is removed, a quarter-turn cleat 313 of the sealing membrane 312 is exposed. The pump 302 is mated to the quarter-turn cleat 313 of the sealing membrane 312 by a twisting motion in which the pump 302 is initially a quarter-turn offset from the retention frame 306, as shown in FIG. 3D, and is then turned to lock the pump 302 in alignment with the frame 306, as shown in FIG. 3E. A similar turn in the opposite direction would be used to detach the pump 302 from the frame 306. Note that although described as a "quarter-turn" cleat, the degree of angular rotation required to lock and unlock the pump 302 from the retention frame can vary. In one embodiment, as depicted in FIG. 3F, the cartridge 316 can include a cleat 317 for mating with the cleat 313 of the sealing membrane 312 and the drive unit 318 can include a corresponding recess 319 to accommodate the cleat 317 when the cartridge 316 and drive unit 318 are mated. Alternatively, the drive unit 318 can include the cleat and the cartridge 316 can define the recess. In a further embodiment, the cleats 313, 317 could further include mating tabbed features that require downward pressure to engage and upward pressure to disengage during rotation of the pump 302, to ensure that an accidental torque on the pump 302 does not dislodge the pump 302 from the frame 306. The connection described in this embodiment utilizing the turnable cleat improves the reliability of the seal between the pump and the frame/infusion site by creating a wiping effect on the water ingress seal located on the cartridge/pump. This connection also preloads the cartridge to bias the cartridge against the pump such that any excessive compliance between the pump and the cartridge is eliminated. This increases the accuracy of the system because any compliance, looseness, or flexing in the connection between the cartridge and the drive unit can lead to delivery inaccuracy in such syringe/lead screw drive pumps.

Figure 4F:
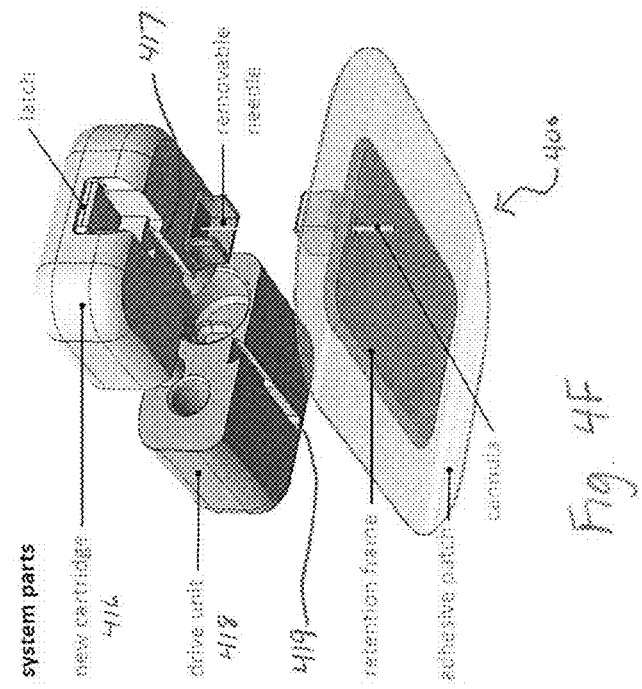
Figure 4E:
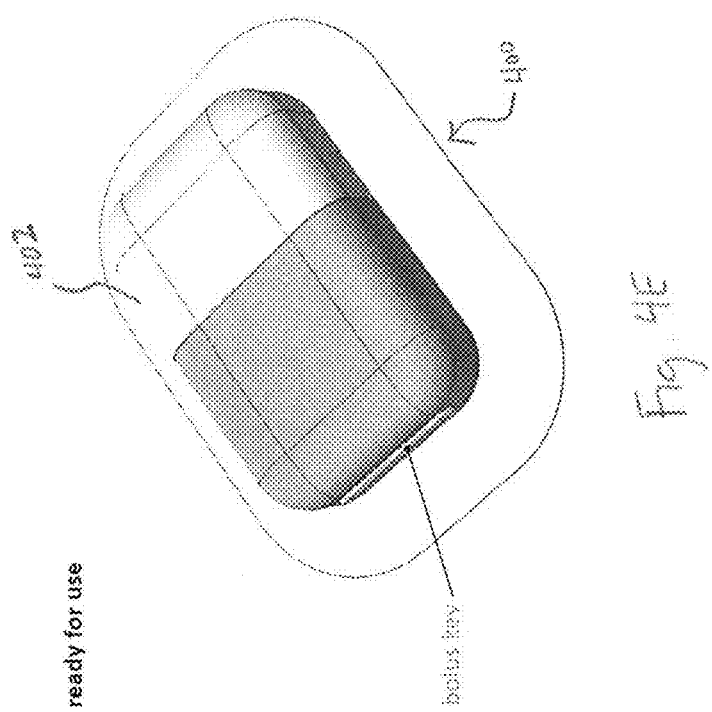
Figure 6A:
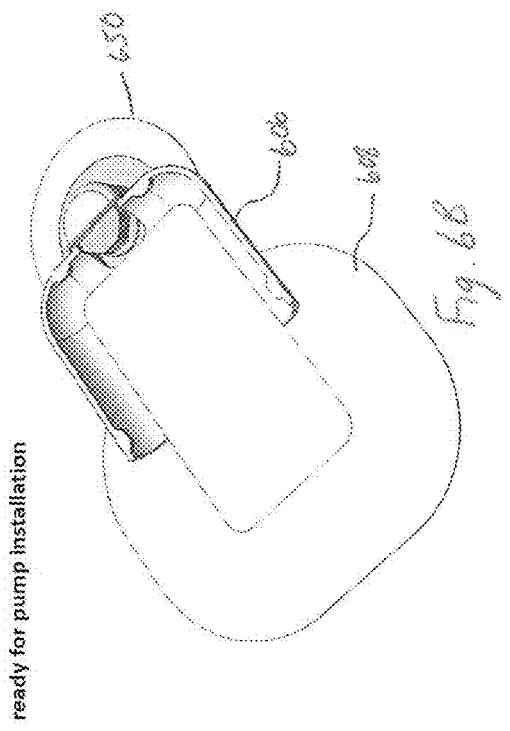
Figure 6B:
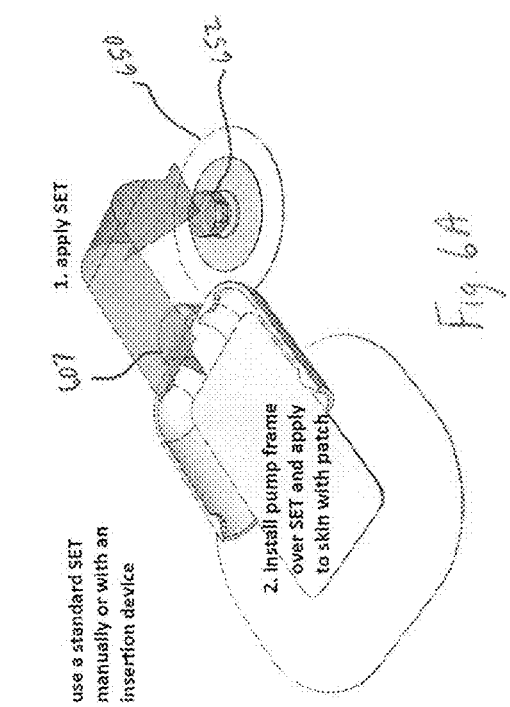
Figure 6C:
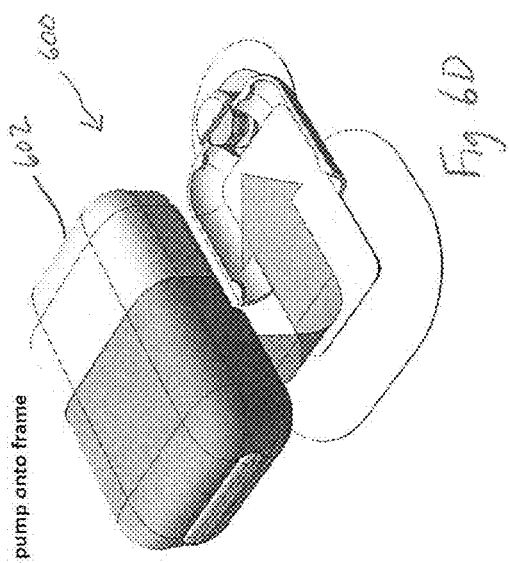
Figure 6D:
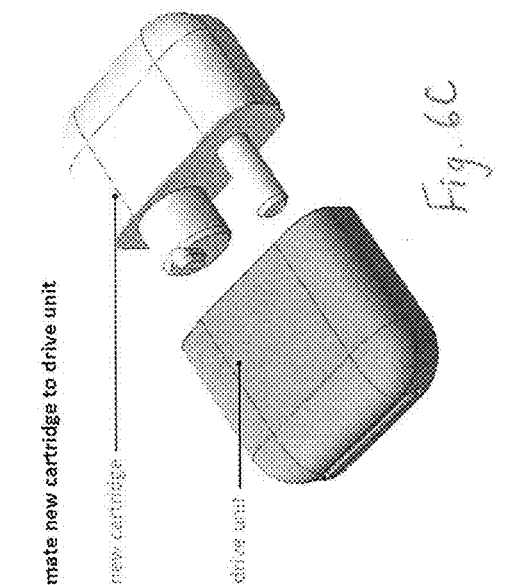
Figure 8B:
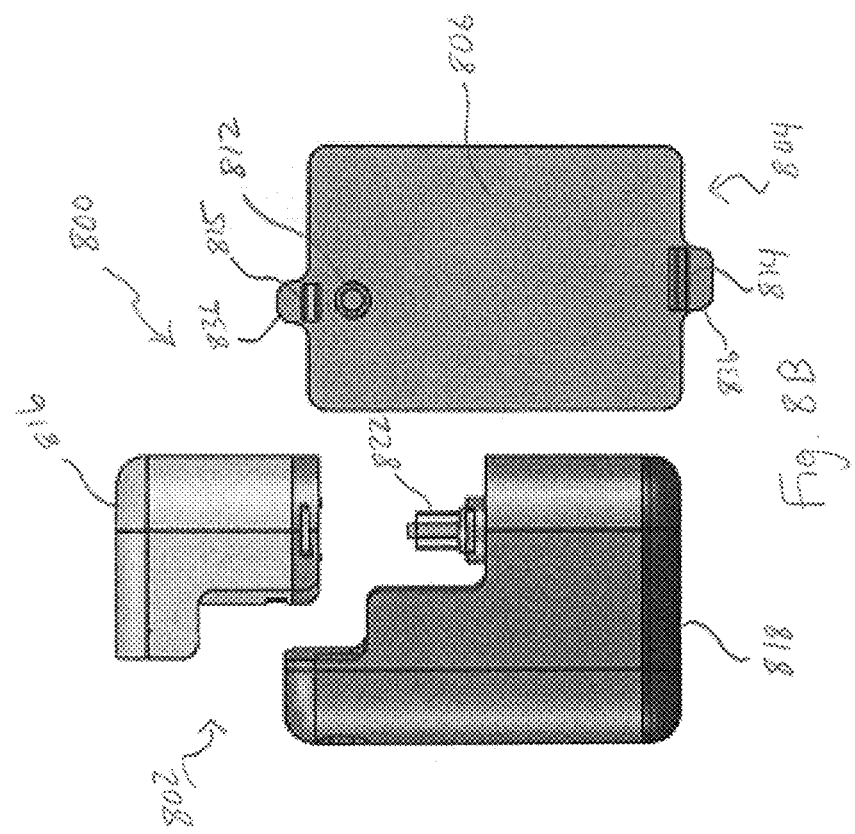
Figure 8A:
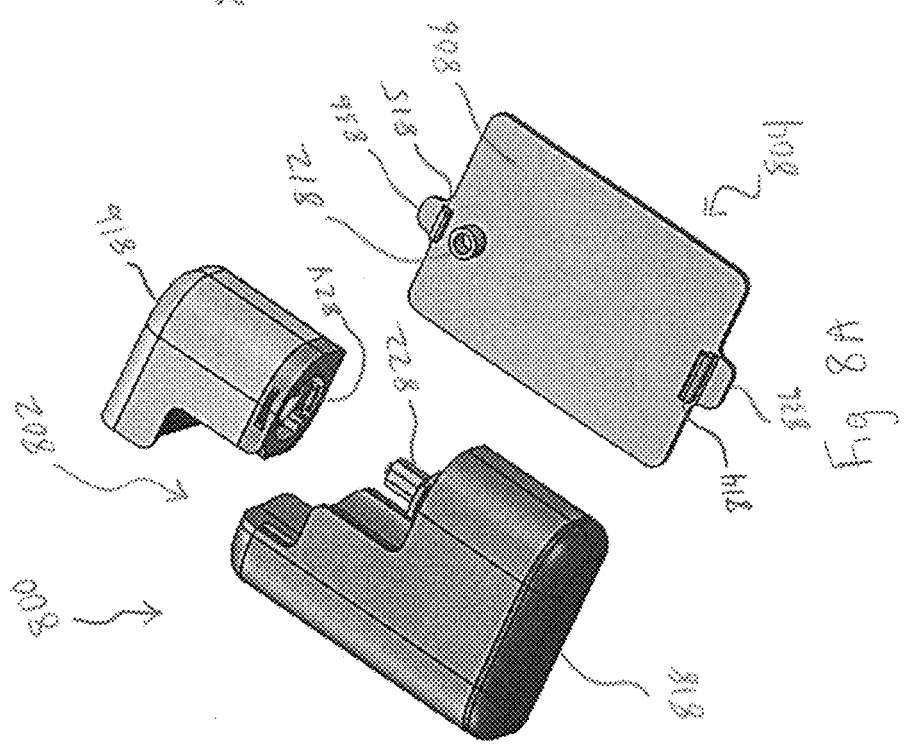

FIGS. 4A-4F depict another embodiment of an insulin patch pump 400 according to an embodiment of the present invention. In this embodiment, the retention frame 406 is again generally flat and includes a rail 407 onto which the pump 402 is slidably inserted. The rail 407 terminates at the sealing membrane 412 to properly align the pump 402 with the sealing membrane 412. As can be seen in FIG. 4F, both the cartridge 416 and the drive unit 418 can include slots 417, 419 that mate with rail 407. Rail 407 can include a leading section 409 that is narrower than the rest of rail 407 to enable the pump 402 to be more easily mated with the retention frame 406. Because the slots 417, 419 of the pump 402 can generally be of constant width, the slot 417 at the leading end of the cartridge 416 will be significantly wider than the leading section 409 of the rail, such that far less precision is needed to initially align the rail 407 with the slots 417, 419. As depicted, pump 402 is held onto retention frame 406 via friction and can be removed with a force applied in the opposite horizontal direction. In some embodiments, retention frame 406 can be provided with tabs that mate with recesses in pump 402, similar to any of the previous embodiments.

FIGS. 5A-5D depict an insulin patch pump 500 according to an embodiment of the present invention in which the location of the infusion site is displaced from the location of the pump 502 and retention frame 506. In this embodiment, a standard infusion set 550 is applied to the skin and the patch pump 500 is affixed nearby with adhesive patch 508. A length of tubing 507 extends between the retention frame 506 and the infusion set 550 through which insulin is delivered from the pump 502 to the set 550. In one embodiment, the tubing 507 is preattached to the retention frame 506. In another embodiment, the tubing 507 is preattached to the cartridge 516 of the pump 502. Such an embodiment would enable the pump 502, when desired, to be used while not being connected to the retention frame 506. In such an embodiment, the retention frame 506 and corresponding adhesive patch 508 could be considered optional. Patch pump 500 can provide the user with the flexibility of applying the infusion set 550 and the patch pump 500 in different locations on the skin or not affixing the patch pump 500 to the skin at all. Although this embodiment is depicted as including features for mating the pump 502 and the retention frame 506 similar to those of FIGS. 2A-2F, it should be understood that the mating features of any of the embodiments described herein could be employed.

Referring now to FIGS. 6A-6E, an embodiment of an insulin patch pump 600 is depicted that is adapted to interface directly with a standard infusion set 650. Initially, the infusion set 650 is applied to the patient's skin. The retention frame 606 of the patch pump 600 defines a receiving slot 607 that interfaces directly with the connector 652 of the infusion set 650 to deliver medicament through a cannula of the infusion set. The receiving slot 607 is therefore then mated with the connector 652 and the adhesive patch 608 of the patch pump 600 is affixed to the skin adjacent the infusion set 650. The pump 602 can then be slid onto the retention frame 606 and mated with both the retention frame 606 and the infusion set connector 652. Again, although this embodiment depicts the pump 602 mating with the frame 606 utilizing features similar to those depicted in FIGS. 2A-2F, it should be understood that any of the mating features described herein could be used, though features that utilize a horizontal sliding action to mate the pump to the frame are advantageous in aligning the cartridge cannula with the infusion set 650. In some embodiments, the retainer frame 606 can be identical to the retainer frame 506, such that the same retainer frame can be used interchangeably either displaced from the infusion site or directly on the infusion site, whether with a standard infusion set or an infusion set as disclosed in previous embodiments. The retainer frames of any other embodiments disclosed herein could similarly be used in an interchangeable fashion between local and remote infusion sites.

FIGS. 8A-8F depict a patch pump 800 including a pump 802 and an attachment portion 804 according to another embodiment of the invention. Retention frame 806 of attachment portion 804 includes an insertion portion 812 through which a disposable needle can be inserted to penetrate a sealing membrane and insert a cannula for medicament delivery, as described previously herein. Drive unit 818 of pump includes a drive mechanism 822 that mates with a recess 824 in disposable cartridge 816 to attach the cartridge 816 to the drive unit 818 and provide for delivery of medicament such as insulin from the cartridge 816 to a user through the cannula.

Retention frame 806 in this embodiment also includes a hook portion 814 adjacent one end of the frame and a snap portion 815 adjacent an opposing end of the frame. To mate the pump 802 with the corresponding attachment portion 804, initially hook portion 814 on retention frame 806 is inserted, or hooked, into a recess 838 in the drive unit 818, as shown in FIGS. 8C and 8D. To complete the insertion and mating process, the pump 802 is pivoted downwardly about the hook portion 814 to mate a recess 839 in cartridge 816 with snap portion 815, as shown in FIGS. 8E and 8F. Snap portion 815 can be flexible and resilient such that when the cartridge 816 is mated with the snap portion 815, the snap portion 815 is initially pushed away from the pump 802 and then snaps into place when aligned with the recess 839 to cause an audible clicking or snapping sound that provides an indication to the user that the pump 802 is properly mated to the attachment portion 806. Pump 802 can be released from attachment portion 804 to, for example, enable a user to exchange the cartridge, with one or more tabs 836, which can be depressed to cause one or both of hook portion 814 and snap portion 815 to withdraw from its corresponding recess in pump 802.

Although various embodiments of the insulin patch pumps described herein include a bolus key 140 for delivering a controlled amount of insulin to the user, in certain embodiments it is primarily intended that such patch pumps will be controlled with a remote device. Remote device can include, for example, a smartphone, an electronic tablet, a computer or a dedicated remote controller. In the case of a smartphone and/or an electronic tablet, a dedicated software application may be provided for control of patch pump. One embodiment of a screen shot of a control screen 700 for a patch pump is depicted in FIG. 7. Control screen 700 can include various information and control functions. The control screen may include, for example, a battery life indicator 702, an indicator 704 that indicates the amount of medicament such as, e.g., insulin remaining in the cartridge, a time and date 706 and an indicator 708 that indicates, in this example, an estimate of the amount of insulin remaining in the user's system as well as the amount of time it will take for that insulin to take effect on the user's blood glucose. One control function available from the control screen 700 is a bolus function 710, the selection of which initiates a programmable bolus delivery with the corresponding patch pump. An options function 712 can allow entry into a menu of additional pump options. Various other information and functions that can be incorporated into and/or utilized by control device are disclosed in the various patents and patent applications incorporated by reference herein.

The embodiments described herein generally include a cartridge and drive unit attached to each other in a generally back-to-back relation such that a body of the cartridge and a body of the drive unit are positioned adjacent to each other to each form all or a portion of the outer housing of the pump. It should be noted, however, that various other attachment configurations of the cartridge and housing are within the scope of the present invention. For example, a body of the cartridge and/or drive unit could be attached by being partially or wholly inserted into or partially or wholly contained within the corresponding component. In one specific embodiment, the cartridge can be wholly contained within the drive unit, and can be accessed through, e.g., a latched cover on the drive unit.

Although the embodiments herein are specifically described with respect to the delivery of insulin, delivery of other medicaments, singly or in combination with one another or with insulin, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, treatment of various conditions including, e.g., pulmonary hypertension, or any other suitable indication or application. Non-medical applications are also contemplated.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Also incorporated herein by reference in their entirety are commonly owned U.S. Pat. Nos. 8,287,495; 8,408,421 and 8,448,824; commonly owned U.S. Patent Publication Nos. 2009/0287180; 2010/0008795; 2010/0071446; 2010/0218586; 2012/0123230; 2013/0053816; 2013/0159456; and 2013/0306191 commonly owned U.S. patent application Ser. Nos. 14/583,274; 14/581,461; 14/581,398; 14/482,521; 14/479,994; 13/800,387; 13/800,453; 13/800,595; 13/801,230; 13/801,274; 13/827,383; 13/827,707; 13/828,958; 13/829,115; 13/832,531; 13/832,841; 13/837,661; 13/837,777; 13/838,084; 13/838,617; 13/841,028; 13/841,432; 13/842,005; 13/842,990 and 13/923,556; and commonly owned U.S. Provisional Application Serial Nos. 61/874,428, 61/875,979, 61/911,576, 61/920,902, 61/920,914, 61/920,923, 61/920,932 and 61/920,940.

Further incorporated by reference herein in their entirety are U.S. Pat. Nos. 8,601,465; 8,502,662; 8,452,953; 8,451,230; 8,449,523; 8,444,595; 8,343,092; 8,285,328; 8,126,728; 8,117,481; 8,095,123; 7,999,674; 7,819,843; 7,782,192; 7,109,878; 6,997,920; 6,979,326; 6,936,029; 6,872,200; 6,813,519; 6,641,533; 6,554,798; 6,551,276; 6,295,506; and 5,665,065. Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

The invention claimed is:

1. A user-wearable infusion pump system, comprising:
  a user-wearable pump including a drive unit and a disposable cartridge selectively attachable to the drive unit, the disposable cartridge configured to contain a medicament and the drive unit configured to cause the pump to deliver the medicament to a user, the user-wearable pump defining an outer perimeter of the user-wearable pump;
  a retention frame configured to selectively retain the user-wearable pump therein, the retention frame including a bottom surface and an outer rim extending upwardly from an outer perimeter of the bottom surface, wherein the outer rim is configured to at least partially surround the outer perimeter of the user-wearable pump when the user-wearable pump is retained in the retention frame;

tubing configured to extend between the user-wearable pump and an infusion site displaced from a location of the retention frame; and a button disposed on the outer perimeter of the user-wearable pump, the button configured to selectively cause the drive unit to cause the pump to deliver a predetermined quantity of medicament when the button is pressed and accessible when the user-wearable pump is retained in the retention frame;

wherein the pump is configured to selectively be put into fluid communication with the tubing to selectively deliver the medicament to the infusion site.

2. The system of claim 1, wherein the pump is slidably received by the retention frame.

3. The system of claim 1, wherein the tubing is integrally attached to the pump.

4. The system of claim 1, wherein the tubing is integrally attached to the disposable cartridge.

5. The system of claim 1, wherein the button is disposed on the drive unit.

6. The system of claim 1, further comprising an adhesive patch affixed to the retention frame and configured to be adhered to the user.

7. The system of claim 1, wherein the outer rim is configured to extend around an entire outer perimeter of the user-wearable pump when the user-wearable pump is retained in the retention frame.

8. The system of claim 1, wherein the outer rim includes a pump retainer extending therefrom, the pump retainer configured to releasably retain the user-wearable pump.

9. The system of claim 8, wherein the pump retainer comprises a pair of tabs extending from the outer rim configured to selectively engage corresponding recesses on the pump to retain the pump on the retention frame.

10. The system of claim 9, wherein a first of the pair of tabs comprises a hook portion and a second of the pair of tabs comprises a snap portion, and the pump is configured to be retained within the retention frame by engaging a first recess of the pump with the hook portion and then engaging a second recess of the pump with the snap portion.

11. The system of claim 8, wherein the pump retainer includes one or more elongate tabs that are slidably received within one or more corresponding elongate recesses in the pump.

12. The system of claim 1, wherein the button is accessible when the user-wearable pump is retained in the retention frame because the button is disposed above the outer rim of the retention frame.

13. The system of claim 1, wherein the button is accessible when the user-wearable pump is retained in the retention frame through an opening in the outer rim of the retention frame.

14. A user-wearable infusion pump system, comprising:

a user-wearable pump including a drive unit and a disposable cartridge selectively attachable to the drive unit, the disposable cartridge configured to contain a medicament and the drive unit configured to cause the pump to deliver the medicament in the cartridge to a user, the user-wearable pump defining an outer perimeter of the user-wearable pump;

a retention frame configured to selectively retain the user-wearable pump therein, the retention frame including a bottom surface and an outer rim extending upwardly from an outer perimeter of the bottom surface, wherein the outer rim is configured to at least partially surround the outer perimeter of the user-wearable pump when the user-wearable pump is retained in the retention frame;

tubing configured to extend between the user-wearable pump and an infusion site displaced from a location of the retention frame; and a button disposed on an outer perimeter of the user-wearable pump, the button configured to selectively cause the drive unit to cause the pump to deliver a predetermined quantity of medicament when the button is pressed and accessible when the user-wearable pump is retained in the retention frame.

15. The system of claim 14, wherein the tubing is integrally attached to the pump.

16. The system of claim 15, wherein the tubing is integrally attached to the disposable cartridge.

17. The system of claim 14, further comprising an adhesive patch affixed to the retention frame and configured to be adhered to the user.

18. The system of claim 14, wherein the outer rim is configured to extend around an entire outer perimeter of the user-wearable pump when the user-wearable pump is retained in the retention frame.

19. The system of claim 14, wherein the outer rim includes a pump retainer extending therefrom, the pump retainer configured to releasably retain the user-wearable pump.

20. The system of claim 19, wherein the pump retainer includes one or more elongate tabs that are slidably received within one or more corresponding elongate recesses in the pump.

21. The system of claim 14, wherein the button is accessible when the user-wearable pump is retained in the retention frame because the button is disposed above the outer rim of the retention frame.

22. The system of claim 14, wherein the button is accessible when the user-wearable pump is retained in the retention frame through an opening in the outer rim of the retention frame.

* * * * *